United States Patent [19]
Krasnansky et al.

[11] Patent Number: 5,922,334
[45] Date of Patent: Jul. 13, 1999

[54] AQUEOUS NAIL COATING COMPOSITION

[75] Inventors: Robert Krasnansky, Le Rouret, France; Curtis Schwartz, Ambler, Pa.

[73] Assignee: Rohm and Haas Company, Philadelphia, Pa.

[21] Appl. No.: 09/073,000

[22] Filed: May 6, 1998

[51] Int. Cl.$^6$ .............................. A61K 6/00; A61K 7/00; A61K 7/04
[52] U.S. Cl. .............................................. 424/401; 424/61
[58] Field of Search ........................................ 424/401, 61

[56] References Cited

U.S. PATENT DOCUMENTS

| | | |
|---|---|---|
| 3,697,643 | 10/1972 | Shepherd et al. . |
| 3,729,569 | 4/1973 | Charle et al. . |
| 3,755,271 | 8/1973 | Montomgery . |
| 3,786,113 | 1/1974 | Vassileff . |
| 3,864,294 | 2/1975 | Busch, Jr. . |
| 4,126,675 | 11/1978 | Boulogne et al. . |
| 4,158,053 | 6/1979 | Greene et al. . |
| 4,178,425 | 12/1979 | Emmons et al. . |
| 4,916,171 | 4/1990 | Brown et al. ............................ 523/161 |
| 5,035,944 | 7/1991 | Frazza et al. . |
| 5,120,529 | 6/1992 | Koch et al. . |
| 5,266,322 | 11/1993 | Myers et al. ............................ 424/401 |
| 5,334,655 | 8/1994 | Carlson et al. . |
| 5,380,520 | 1/1995 | Dobbs . |
| 5,428,107 | 6/1995 | Tysak et al. . |

FOREIGN PATENT DOCUMENTS

| | | |
|---|---|---|
| 450416 | 3/1984 | Canada . |
| 061348 | 3/1982 | European Pat. Off. . |
| 3931237A1 | 6/1990 | Germany . |
| 4-103511 | 4/1992 | Japan . |
| 4-103513 | 4/1992 | Japan . |
| 5-92558 | 10/1994 | Japan . |
| 6-17816 | 10/1994 | Japan . |
| 6-279239 | 10/1994 | Japan . |
| 6-298624 | 10/1994 | Japan . |

OTHER PUBLICATIONS

"Advances in Nail Enamel Technology", J. Soc. Cosmet. Chem. 43, 331–337 (Nov./Dec. 1992), M. Schlossman and E. Wimmer.

"Polymers and Thickeners in Nail–Care Products", by Harvey M. Remz, Cosmetics & Toiletries, vol. 103, Dec. 1988.

*Primary Examiner*—Johann Richter
*Assistant Examiner*—Sharon Howard
*Attorney, Agent, or Firm*—Kimberly R. Hild

[57] ABSTRACT

The present invention provides an aqueous nail coating composition containing a dispersion of multi-phase polymers. The aqueous nail coating composition has improved resistance to abrasion and chemicals.

12 Claims, No Drawings

AQUEOUS NAIL COATING COMPOSITION

FIELD OF INVENTION

The present invention relates to an aqueous nail coating composition which forms a film on nails having improved resistance to abrasion and chemicals.

BACKGROUND

Various types of nail coating compositions are used by consumers today. By "nail coating composition" we mean a coating useful on nails for such purposes as changing the cosmetic appearance of nails, strengthening nails and hardening nails. Nail coating compositions include for example nail polishes, nail lacquers, top coats, base coats, nail strengtheners, nail hardeners, and nail polish quick dry products. Nail coating compositions typically contain one or more film formers in combination with other formulation additives such as solvents, coalescent agents, plasticizers, thickeners, suspension aids, and pigments.

One of the most popular film formers used today in nail coating compositions is nitrocellulose. Nitrocellulose is typically used in nail coating compositions as a primary film former in combination with a secondary film former such as toluene sulfonamide formaldehyde. The secondary film former is added to the nail coating composition to improve such properties as application, wear, and gloss. Although nitrocellulose has excellent pigment wetting capabilities, and forms a film which dries quickly, has high gloss, good hardness, and good resistance to abrasion and chemicals, it has disadvantages. For example, formulations containing nitrocellulose tend to discolor the nails and over time tend to drop in viscosity and lose the ability to form a hard film. Also, for solubility reasons, nitrocellulose is undesirably formulated with organic solvents such as ethyl acetate, methyl ethyl ketone, and toluene. These organic solvents are undesirable because they tend to be flammable and adversely affect air quality. Organic solvents also tend to discolor the nails, and make them brittle.

Because of these problems, nail formulators have investigated developing film formers for use in aqueous nail coating compositions. Most approaches have involved using a blend or dispersion of polymers which will form a film from an aqueous medium. For example, polyurethanes and polyacrylates have been used in aqueous nail coating compositions. However, these polymers tend to have inferior pigment wetting properties, and tend to form films which are not as durable, and have poor resistance to chemicals and abrasion.

JP 06-298624A has attempted to overcome these deficiencies of aqueous nail coating compositions by using as a film former an emulsion of dispersed particles having two polymer phases. The aqueous emulsion contains an inner A-phase polymer prepared from at least one type of monomer selected from alkyl methacrylic acid esters, aromatic vinyl compounds or monomers having two or more polymerizable unsaturated groups. The outer B-phase polymer consists of a copolymer prepared from at least one monomer selected from alkyl methacrylic acid esters, aromatic vinyl compounds, or monomers having two or more polymerizable unsaturated groups, and at least one type of monomer selected from a monomer containing a hydroxyl group, or amide group. The B-phase polymer has a weight average molecular weight of 200,000 or greater.

However, JP 06-298624A does not disclose that by controlling the degree of hydrophobicity in the polymer phases, an aqueous nail coating composition can be produced which has improved resistance to chemicals and abrasion. JP 06-298624A also does not address the problem of removeability of aqueous nail coating compositions. As detailed herein, removeability of aqueous nail coating compositions with conventional nail polish removers has been a problem. More particularly, improving removeability of an aqueous nail coating composition, without adversely affecting the chemical and abrasion resistance of the coating has been difficult.

Therefore, it is desirable to provide an aqueous nail coating composition which has improved resistance to chemicals and abrasion. It is also preferable to provide an aqueous nail coating composition which has improved removeability. The present invention addresses these problems by incorporating into an aqueous nail coating composition a film forming agent containing certain multi-phase polymers.

STATEMENT OF INVENTION

The present invention provides an aqueous nail coating composition comprising: at least one film forming agent comprising a dispersion of multi-phase polymers; wherein the multi-phase polymers comprise at least one inner polymer phase and at least one outer polymer phase; wherein the inner polymer has a Tg of at least 30° C. and comprises as polymerized units at least 2 weight percent of a hydrophobic monomer, based on total weight of monomer in the inner polymer; wherein the outer polymer has a Tg from −15° C. to 35° C., and comprises as polymerized units at least 3 weight percent of a second hydrophobic monomer; wherein the weight ratio of the inner polymer to the outer polymer is from 20:80 to 70:30; and provided that when the outer polymer has a weight average molecular weight equal to or greater than 200,000, the inner polymer further comprises at least 0.01 weight percent crosslinking agent based on total monomer in the inner polymer, and the outer polymer has a soluble fraction in tetrahydrofuran of at least 15 weight percent, and comprises from 3 weight percent to 70 weight percent of the second hydrophobic monomer based on total monomer in the outer polymer.

DETAILED DESCRIPTION

The aqueous nail coating composition of the present invention contains at least one film forming agent. By "aqueous", we mean the nail coating composition contains at least 35 weight percent, preferably from 45 weight percent to 90 weight percent, and most preferably from 45 weight percent to 55 weight percent water.

The nail coating composition is preferably intended for use on nails. For example, the nail coating composition can be a nail polish, nail lacquer, top coat, base coat, nail strengthener, nail hardener, or nail polish quick dry product.

The film forming agent in the nail coating composition is a dispersion of multi-phase polymer particles having at least one inner or "core" polymer phase and at least one outer or "shell" polymer phase. The phases of the polymers are incompatible. By "incompatible", we mean that the core and shell polymer phases are distinguishable using techniques known to those skilled in the art. For example the use of scanning electron microscopy and staining techniques to emphasize differences in phases is such a technique.

The morphological configuration of the phases of the polymers may be for example, core/shell, core/shell particles with shell phases incompletely encapsulating the core, core/shell with a multiplicity of cores, or interpenetrating network particles. We have found that the film forming agent having at least one core phase and at least one shell phase imparts a better balance of properties to the nail coating composition in comparison to a film former containing only one polymer phase.

The phases of the polymers are preferably formed through the sequential emulsion polymerization of ethylenically unsaturated monomers by techniques well known to those skilled in the art. For example, the aqueous dispersion of polymers can be prepared by processes disclosed in U.S. Pat. Nos. 4,325,856, 4,654,397, and 4,814,373.

Ethylenically unsaturated monomers which can be sequentially emulsion polymerized to form the phases include for example (meth)acrylic ester monomers such as methyl (meth)acrylate, ethyl (meth)acrylate, butyl (meth) acrylate such as i-butyl (meth)acrylate, or t-butyl (meth) acrylate, 2-ethylhexyl (meth)acrylate, decyl (meth)acrylate, i-bornyl (meth)acrylate, hydroxyethyl (meth)acrylate, hydroxypropyl (meth)acrylate; aromatic vinyl compounds such as styrene, substituted styrenes; butadiene; acrylonitrile; monomers containing acetoacetoxy functional groups such as acetoacetoxyethyl methacrylate; vinyl acetate; acid or base containing monomers such as, for example, (meth) acrylic acid, itaconic acid, maleic acid, fumaric acid, N,N-dimethylaminoethyl methacrylate; or combinations thereof. Additionally, crosslinking and grafting monomers such as 1,4-butyleneglycol methacrylate, trimethylolpropane triacrylate, allyl methacrylate, diallyl phthalate, divinyl benzene, or combinations thereof may be used. As used herein, by "(meth)acrylate" or "(meth)acrylic", we mean either acrylate or methacrylate for "(meth)acrylate" and acrylic or methacrylic for "(meth)acrylic".

The polymer composition and molecular weight of each phase is selected to impart a balance of properties to the aqueous nail coating composition. Such properties to consider include for example film forming quality, removeablitiy, and resistance to chipping, peeling, print, chemicals, and water.

The polymer composition and molecular weight of the core phase is preferably chosen to impart hardness and chemical resistance to the aqueous nail coating composition. The core phase is preferably a copolymer containing two or more different monomers. Hardness is typically achieved through the polymerization of monomers with relatively high glass transition temperatures (Tg). Chemical resistance is preferably achieved through controlling the degree of hydrophobicity of the core polymer phase.

The core polymer phase has a glass transition temperature (Tg) of at least 30° C., preferably at least 35° C., more preferably at least 40° C., and most preferably from 45° C. to 120° C. As used herein, the Tg of a polymer phase is calculated by Equation 1:

$$Tg = \sum_i (W_i Tg_i) \qquad \text{Equation 1}$$

where $W_i$=weight fraction of monomer i in the polymer $Tg_i$=the glass transition temperature of a homopolymer of monomer i.

The core polymer phase preferably has a weight average molecular weight (Mw) of from 500,000 to 10,000,000. In order to regulate molecular weight of the core phase, chain transfer agents such as for example mercaptans, polymercaptans, alcohols, and polyhalogens may be used. Specific examples of chain transfer agents include for example t-dodecyl mercaptan, 3-mercaptoproprionic acid, isopropanol, isobutanol, lauryl acohol, carbon tetrachloride, or tetra chlorobromoethane, or combinations thereof.

The core polymer phase contains at least 2 weight percent of at least one hydrophobic monomer. Preferably the core polymer phase contains from 4 weight percent to 95 weight percent; more preferably from 10 weight percent to 90 weight percent and most preferably from 15 weight percent to 80 weight percent hydrophobic monomer. By "hydrophobic monomer," we mean ethylenically unsaturated monomers which have a solubility in water of about equal to or less than 1 gram per 100 grams of water at 20° C. Hydrophobic monomers include for example alkyl (meth)acrylates with the alkyl substituent having 4 or more carbon atoms, and preferably from 4 to 18 carbon atoms. Suitable alkyl (meth)acrylates include for example butyl (meth)acrylate, 2-ethylhexyl (meth)acrylate, decyl (meth)acrylate, butyl (meth)acrylate such as i-butyl (meth)acrylate, or t-butyl (meth)acrylate, or i-bornyl (meth)acrylate, or combinations thereof. Hydrophobic monomers also include for example aromatic vinyl compounds such as styrene, substituted styrenes, vinyltoluene; or aliphatic conjugated diene monomers containing 4 to 18 carbons such as butadiene, pentadiene, hexadiene; or combinations thereof. Preferably, the hydrophobic monomers are $C_4$ to $C_{10}$ .alkyl (meth) acrylates, or aromatic vinyl compounds; and more preferably butyl (meth)acrylate, i-butyl (meth)acrylate, i-bornyl (meth)acrylate, 2-ethylhexyl (meth)acrylate, styrene, or combinations thereof.

Preferably, the core polymer phase contains at least one crosslinking agent. As detailed hereinafter, the addition of the crosslinking agent to the core polymer phase provides improved resistance to abrasion and chemicals. The crosslinking agent is preferably added in an amount of at least 0.01 weight percent, more preferably from 0.05 weight percent to 20 weight percent, and most preferably from 0.1 weight percent to 10 weight percent, based on the total weight of monomer in the core polymer phase. In order to provide removeability, the level of crosslinking agent added to the core phase is preferably in an amount to provide a polymer with an overall solubility fraction in tetrahydrofuran (THF) at ambient temperature (22±4° C.) of at least 15 weight percent, more preferably from 20 weight percent to 95 weight percent, and most preferably from 22 weight percent to 80 weight percent. Suitable crosslinking agents include for example 1,4-butyleneglycol dimethacrylate, trimethylolpropane triacrylate, allyl methacrylate, diallyl phthalate, divinylbenzene or trivinylbenzene or combinations thereof. Preferably, the crosslinking agent, if present, is allyl methacrylate.

The shell polymer phase is a copolymer containing two or more different ethylenically unsaturated monomers as polymerized units. The shell polymer composition and molecular weight is preferably chosen to enhance film formation and chemical resistance. Film formation is enhanced through the use of monomers whose homopolymers have Tgs below about 40° C. Film formation can also be enhanced through controlling the molecular weight of the shell polymer phase.

Preferably, the shell polymer phase has a Tg from −15° C. to 35° C., and more preferably from −5 to 30° C. It is also preferred that the core polymer phase have a higher Tg than the shell polymer phase.

The shell polymer phase preferably has a weight average molecular weight (Mw) which enables the shell polymer to have a soluble fraction in THF at ambient temperature of at least 15 weight percent, more preferably from 30 to 100 weight percent, and most preferably from 60 to 100 weight percent. The shell polymer molecular weight is preferably equal to or less than 5,000,000, more preferably less than or equal to 190,000, and most preferably from 10,000 to 175,000, based on a polymethyl methacrylate standard having a Mw of 100,000.

In order to regulate the molecular weight of the shell polymer phase, chain transfer agents are preferably used. Suitable chain transfer agents include for example mercaptans, polymercaptans, alcohols, and polyhalogens. Preferable chain transfer agents are t-dodecyl mercaptan, 3-mercaptoproprionic acid, isopropanol, isobutanol, lauryl alcohol, carbon tetrachloride, or tetra chlorobromoethane, or combinations thereof. Preferably, the chain transfer agent is used at a level from about 0.01 weight percent to 5 weight percent and more preferably at a level of from 0.25 weight percent to 3 weight percent based on total weight of monomer in the shell polymer phase.

The shell polymer phase contains, based on the total weight of monomer in the shell, at least 3 weight percent of at least one hydrophobic monomer, where hydrophobic monomer has the same meaning as defined previously herein. More preferably the shell polymer phase contains from 3.0 weight percent to 70.0 weight percent, and most preferably from 5.0 weight percent to 59.9 weight percent of hydrophobic monomer, based on the total weight of monomer in the shell. The hydrophobic monomer selected for the shell polymer phase may be the same or different from those used in the core polymer phase. Preferable hydrophobic monomers in the shell polymer phase are $C_4$–$C_{10}$ alkyl (meth)acrylates, aromatic vinyl compounds, or combinations thereof; and more preferably butyl (meth)acrylate, i-butyl (meth)acrylate, i-bornyl (meth)acrylate, 2-ethylhexyl (meth)acrylate, styrene, or combinations thereof.

The polymer particles preferably contain as the core polymer phase from 20 parts by weight to 70 parts by weight, more preferably from 24 parts by weight to 65 parts by weight, and most preferably from 40 parts by weight to 60 parts by weight core polymer phase based on 100 parts polymer particles. The polymer particles preferably contain as the shell polymer 30 parts by weight to 80 parts by weight; more preferably, from 35 parts by weight to 76 parts by weight, and most preferably from 40 parts by weight to 60 parts by weight based on 100 parts by weight polymer particles.

The particle size of the polymer particles is preferably from 75 nanometers to 500 nanometers, more preferably from 100 nanometers to 400 nanometers and most preferably from 150 nanometers to 300 nanometers as measured by a Brookhaven BI-90 Particle sizer which employs a light scattering technique.

In one embodiment of the present invention, when the shell polymer Mw is equal to or greater than 200,000, the multi-phase polymer preferably contains a core polymer having at least 0.01 weight percent crosslinking agent, and a shell polymer having a solubility fraction in THF of at least 15 weight percent at ambient temperature. It is also preferable in this embodiment that the shell polymer contain from 3 weight percent to 70 weight percent of at least one hydrophobic monomer, based on total weight of monomer in the shell polymer.

In a second embodiment of the present invention, the multi-phase polymers contain as polymerized units at least one ethylenically unsaturated acid containing monomer. Preferably the weight of acid containing monomer in the polymers, based on total weight of monomer polymerized in the polymers is from 0.5 weight percent to 25 weight percent, more preferably from 2 weight percent to 10 weight percent, and most preferably from 4 weight percent to 6 weight percent. Suitable acid containing monomers include for example monoethylenically unsaturated mono, di, or polycarboxylic acids such as (meth)acrylic acid, crotonic acid, aconitic acid, itaconic acid, maleic acid, fumaric acid, or the partial esters or anhydrides thereof; or combinations thereof. Preferably (meth)acrylic acid is used as the acid containing monomer.

In a third embodiment of the present invention, the multi-phase polymers contain pendant acetoacetate groups, alternatively known as beta-ketoesters. The term "pendant" as used herein means attached to the polymer backbone and includes acetoacetate groups attached at the termini of the polymer chain. Polymers having acetoacetate functionality can be made for example by using chain transfer agents which contain the acetoacetate functionality such as for example an acetoacetate functional mercaptan as taught in U.S. Pat. No. 4,960,924, or monomers containing the acetoacetate functionality. A preferred monomer is acetoacetoxyethyl methacrylate (AAEM). Other monomers which are useful for introduction of the acetoacetate functionality are acetoacetoxyethyl acrylate, acetoacetoxypropyl methacrylate, allyl acetoacetate, acetoacetoxybutyl methacrylate, 2,3-di(acetoacetoxy) propyl methacrylate or combinations thereof. In general, any polymerizable hydroxy-functional monomer can be converted to the corresponding acetoacetate by reaction with diketene or other suitable acetoacetylating agent (see e.g., Comparison of Methods for the Preparation of Acetoacetylated Coating Resins, Witzeman, J. S.; Dell Nottingham, W.; Del Rector, F. J. Coatings Technology; Vol. 62, 1990, p. 101, and references contained therein). Preferably the polymers contain as polymerized units from 0 to 20 weight percent of acetoacetate functional compounds, more preferably from 2 to 15 and most preferably from 5 to 10 based on total weight of monomer.

In addition to the film forming agent, the aqueous nail coating composition preferably contains at least one coalescent agent. The coalescent agent is added to enhance film formation. Preferably the coalescent agent is added at a level of from 2 weight percent to 45 weight percent, more preferably from 10 weight percent to 30 weight percent, and most preferably from 15 weight percent to 25 weight percent based on the total film forming agent in the nail coating composition. Suitable coalescent agents are for example nonionic or anionic. Preferably the coalescent agents are nonionic. Suitable coalescent agents include for example alkylene glycol alkyl ethers such as butyl Cellosolve® (registered trademark of Union Carbide), hexyl Cellosolve, methyl Carbitol® (registered trademark of Union Carbide), butyl Carbitol, or hexyl Carbitol; aromatic glycol ethers; alkyl polyglucosides; polysiloxanes including ethoxylated polysiloxanes, such as Dimethicone, Dimethiconecopolyol, or phenyl trimethicone; alcohols such as n-propanol, isopropanol, or benzyl alcohol; or alkyl ester acetates. Preferably, the coalescent agent is an alkylene glycol alkyl ether.

Preferably the nail coating composition also contains a neutralizer when acidic or basic groups are present in the film forming agent to promote solubility of the film forming agent in water. The neutralizer is preferably added at a level to neutralize at least 10 mole percent, more preferably at least 60 mole percent, and most preferably 100 mole percent of the acidic or basic groups, based on the total moles of acidic or basic groups in the film forming agent. Suitable neutralizers include for example amines, alkali or alkaline earth metal hydroxides, ammonium hydroxide or combinations thereof. Suitable amine neutralizers include for example 2-amino-2-methyl propanediol, 2-amino-2-methylpropanol, N,N-dimethyl-2-amino-2-methyl-1-propanol, mono-isopropanolamine, triisopropanolamine, ethanolamine, triethanolamine, morpholine or combinations thereof. Suitable alkali or alkaline earth metal hydroxides include for example sodium hydroxide, potassium hydroxide, ammonium hydroxide, or combinations thereof. Preferably, the neutralizer is selected from the group consisting of 2-amino 2-methyl propanediol, 2-amino-2-methylpropanol, N,N-dimethyl-2-amino-2-methylpropanol, ammonium hydroxide, potassium hydroxide, triethanolamine, triisopropanolamine, or combinations thereof, and more preferably the neutralizer is ammonium hydroxide.

Optionally, other additives, such as additional film forming agents, rheology modifiers, thickeners, or solvents may be added to the aqueous nail coating composition. Optional additives preferably comprise from 0.05 weight percent to 25 weight percent, more preferably from 0.1 weight percent to 7 weight percent and most preferably from 0.2 weight percent to 2 weight percent based on the total weight of the nail coating composition. Overall, the aqueous nail coating composition preferably contains from 10 weight percent to 65 weight percent, and more preferably from 20 weight percent to 40 weight percent solids.

Additional film forming agents, when present, preferably comprise from 1 weight percent to 15 weight percent, more preferably from 5 weight percent to 10 weight percent based on the total weight of the aqueous nail coating composition. The additional film forming agents may be primary or secondary. Suitable film forming agents include for example homopolymers or copolymers of $C_1$ to $C_{18}$ alkyl or aryl (meth)acrylates, $C_1$–$C_{18}$ hydroxyalkyl (meth)acrylates; maleic anhydride; (meth)acrylic acid; alkyl vinyl ethers; ethyleneimine, diethyleneglycol monoacrylate; styrene; substituted styrene; acrylamide; substituted acrylamide; methylcellulose; or hydroxypropyl cellulose.

Rheology modifiers or thickeners which may be added to the aqueous nail composition preferably comprise from 0.05 weight percent to 10 weight percent, and more preferably from 0.2 weight percent to 3 weight percent, based on the total weight of the aqueous nail coating composition. Suitable thickeners or rheology modifiers include for example hydrophobically modified nonionic ethoxylated urethanes, or polycarboxylic acid thickeners such as acrylates/steareth-20 methacrylate copolymer, carbomers, acrylates copolymer, or acrylates $C_{10\text{-}30}$ alkyl acrylate crosspolymer. Preferably, the thickeners or rheology modifiers are the hydrophobically modified nonionic ethoxylated urethanes. Preferable ethoxylated urethanes are copolymers of polyalkylene glycols and diisocyanates that are capped with a $C_5$ to $C_{20}$ hydrophobe, polyether alcohol, or combinations thereof. Hydrophobically modified ethoxylated urethanes include Aculyn® 44 (registered trademark of Rohm and Haas Company) and Aculyn 46.

Solvents may optionally be added to the aqueous nail composition at a level of from 5 to 50 weight percent. Suitable solvents include for example $C_1$ to $C_{12}$ straight or branched chain alcohols such as ethanol, isopropanol, or propanol; alkyl esters such as ethyl acetate; ketones; or combinations thereof.

Other optional additives include plasticizers such as dioctyl phthalate; antifoaming agents; leveling aids; pigments; pigment dispersants; UV absorbers; surfactants; nail conditioning agents such as hydrolyzed keratin, hydrolyzed lecithin, isostearyl hydrolyzed collagen; preservatives; slip aids such as carnuba wax, bees wax paraffin, or synthetic wax; antioxidants; suspending agents such as diatomaceous earth, bentonite, montmorillonite, hectorite, or smectite; or coloring agents. Further examples of optional additives mentioned herein and other optional additives which may be added to the aqueous nail coating composition may be found in the International Cosmetic Ingredients Dictionary, 5th Edition, 1993, published by the CTFA in Washington D.C.

EXAMPLES

Some embodiments of the invention will now be described in detail in the following Examples.

In the Examples, the weight average molecular weight (Mw) of the shell polymer phase was determined by synthesizing the shell polymer phase, without synthesizing the inner polymer phase. The Mw of the shell polymer phase was measured by gel permeation chromatography using poly(methylmethacrylate) having a Mw of 100,000 as a standard and distilled THF as the elution solvent.

The soluble fraction of the multi-phase polymers or shell polymers was determined as follows: The polymer to be evaluated was added to a 1 ounce vial in an amount to provide about 0.50 grams of polymer solids. Approximately 20 to 25 milliliters of tetrahydrofuran (THF) was then added, and the solution was shaken overnight at ambient temperature. Following shaking, approximately 1 gram of the solution was taken from the vial and placed in a tared aluminum drying pan to measure the initial weight percent solids (% Initial Polymer Solids) of the solution. The percent solids of the solution was determined by evaporating the THF, drying the sample at 150° C. for 30 minutes, and measuring the weight of polymer in the drying pan. The % Initial Polymer Solids was determined by dividing the weight of polymer in the drying pan by the weight of solution placed in the drying pan.

About 6 grams of the solution in the vial was charged to a centrifuge tube and centrifuged using a Sorvall OTD65B refrigerated ultra-centrifuge at a speed of 50,000 RPM and at a temperature of 10° C. to 15° C. for two hours and 40 minutes. The supernate from the centrifuge was then placed in a tared aluminum drying pan to measure the weight of solids in the supernate. The soluble fraction was calculated as shown in Equation 2:

$$\text{Soluble Fraction} = \left( \frac{\text{Weight of Supernate Solids}}{\text{Weight of Solids Charged to Tube}} \right) \times 100 \quad \text{Equation 2}$$

The Weight of Solids Charged to Tube in Equation 2 was determined by multiplying the % Initial Polymer Solids by the weight of solution charged to the centrifuge tube.

The following abbreviations are used in the Examples:

TABLE 1

Abbreviations

| Abbreviation | Meaning |
| --- | --- |
| AAEM | weight percent acetylacetoxyethylmethacrylate |
| BA | weight percent butyl acrylate |
| DI | Deionized |
| DVB | weight percent divinylbenzene |
| EA | weight percent ethyl acrylate |
| EHA | weight percent 2-ethylhexylacrylate |
| MA | methylacrylate |
| MAA | weight percent methacrylic acid |
| MMA | weight percent methyl methacrylate |
| pbw | parts by weight |
| SDS | sodium dodecyl benzene sulfonate |
| STY | weight percent styrene |
| ALMA | weight percent allylmethacrylate |
| MPA | weight percent 3-mercaptopropionic acid |

Example 1

Synthesis of Multi-Phase Polymers

To a 3 liter, 4 neck round bottom flask with overhead stirrer, coil condenser, nitrogen adapter and a thermocouple containing 657.4 grams (g) DI water, and 20 g of SDS (23 weight percent active SDS) which had been heated to 85° C. was added 28 g of Monomer Emulsion #1 (ME #1). Residual ME #1 was then rinsed into the flask with 20 g DI water. A solution of 1.35 g of ammonium persulfate in 20 g DI water and a solution of 1.4 g sodium carbonate in 40 g DI water were added. The reaction mixture was held at a temperature of 83° C. for five minutes. After the five minute hold, the remainder of ME #1 and a solution of 1.35 g ammonium persulfate in 135 g DI water were linearly fed into the flask over 75 minutes and 160 minutes respectively. After 75 minutes, residual ME #1 was rinsed into the flask with 20 g DI water. After the completion of the rinse, Monomer Emulsion #2 (ME #2) was fed into the flask over 75 minutes. Residual ME #2 was rinsed into the flask with 20 g DI water. When the initiator feed was complete, the reaction mixture was held at 83° C. for 20 minutes. Following the hold, the reaction mixture was cooled to 60° C. and chased over 30 minutes to remove residual monomer. The final reaction mixture was neutralized to pH=7.8 with 28 weight percent aqueous ammonia. The final dispersion of polymers had a solids content of 40.8 weight percent and a particle size of 101 nanometers.

TABLE 1

| Monomer Emulsion #1 | |
| --- | --- |
| DI water | 135 g |
| SDS (23 weight percent active) | 12 g |
| Butyl Acrylate | 99 g |
| Methyl methacrylate | 339.8 g |
| Allyl methacrylate | 2.23 g |
| Methacrylic acid | 9.0 g |
| Total | 597.03 g |
| Monomer Emulsion #2 | |
| DI water | 135 g |
| SDS (23 weight percent active) | 12 g |

TABLE 1-continued

| Methyl methacrylate | 146.3 g |
| --- | --- |
| Methacrylic acid | 36 g |
| 2-Ethylhexyl acrylate | 184.5 g |
| Styrene | 11.2 g |
| Acetoacetoxyethyl methacrylate | 72 g |
| 3-Mercaptopropionic acid | 1.33 g |

Example 2

Comparative—One Polymer Phase

To a 3000 ml, 4 neck round bottom flask with overhead stirrer, coil condenser, nitrogen adapter and a thermocouple, were added 657.4 g DI water and 20.0 g SDS (23 weight percent active). This mixture was stirred and heated to 85° C. under a nitrogen sweep using a heating mantle. Next, to the flask was added 28 grams of a monomer emulsion (ME) consisting of 270.0 g DI water, 24.0 g SDS (23 weight percent active), 99.0 g of butyl acrylate, 484.2 g of methyl methacrylate, 4.5 g of allyl methacrylate, 45.0 g of methacrylic acid, 184.5 g 2-ethyl hexyl acrylate, 10.8 g styrene, 72.0 g acetoacetoxyethyl methacrylate and 1.31 g mercaptopropionic acid. Residual ME was rinsed into the flask with 20 g DI water. The nitrogen sweep was turned off; and to the flask was added an initiator solution consisting of 1.35 g ammonium persulfate in 20.0 g DI water, and a solution consisting of 1.4 g sodium carbonate in 40.0 g DI water. The temperature of the mixture was adjusted to 83 ° C. and the mixture was held for 5 minutes. After the hold, the remaining ME was fed into the flask over 150 minutes, and at the same time an initiator solution of 1.35 g ammonium persulfate in 135.0 g DI water was cofed into the flask over 160 minutes. After the ME feed was complete, residual ME was rinsed into the flask with 40.0 g DI water. When the initiator feed was complete, the mixture was held at 83° C. for 20 minutes and then cooled to 60° C. Following cooling to 60° C., the mixture was chased to remove residual monomer over a 30 minute time period. The mixture was then cooled to room temperature and neutralized with a solution of 13.7 g ammonium hydroxide (28 weight percent active) and 13.7 g DI water. The final polymer had a solids content of 39.1 weight percent, a pH of 8.0 and a particle size of 86 nanometer.

Example 3

Comparative

A two phase polymer was prepared according to Example 3 in JP 06-298624A. To a two liter, four neck, round bottom flask equipped with overhead stirrer, coil condenser, nitrogen adapter and a thermocouple were added 309.0 g of DI water, and 6.53 g SDS (23.0 weight percent active). This mixture was heated with stirring to a temperature of 70° C. under nitrogen sweep. Next, an initiator solution of 1.5 g potassium persulfate in 10.0 grams DI water was added with stirring at 70° C. After the initiator solution was charged, Monomer Emulsion Feed #1a, consisting of 83.32 g DI water, 2.18 g SDS (23.0 weight percent active), 186.0 g methyl methacrylate, 59.0 g butyl acrylate and 5.0 g divinyl benzene was fed at a rate of 2.8 grams/minute over 120 minutes. After Monomer Emulsion Feed #1a was complete, the reaction mixture was held at 70° C. for 60 minutes. Following the hold, Monomer Emulsion Feed #2a, consisting of 78.32 g DI water, 2.18 g SDS (23.0 weight percent active), 141.5 g styrene, 83.5 g butyl acrylate, 10.0 g acrylamide (50 weight percent active), 10.0 g 2-hydroxyethyl methacrylate, 10.0 g methacrylic acid and 0.25 g t-dodecyl mercaptan, was fed at a rate of 2.8 g/minute for a total of 120 minutes. Following the completion of Monomer Emulsion Feed #2a, the reaction mixture was held at 70° C. for 60 minutes. During this last hold, the reaction mixture formed into a solid gel ball.

Examples 5–24

Dispersions of polymers were made according the procedure in Example 1 except that the core:shell weight ratios, and core and shell compositions were varied as follows:

TABLE 2

Polymer Compositions

| Example | Wt Core: Shell[1] | Core Composition (wt %, based on total weight of monomer) | Shell Composition (wt %, based on total weight of monomer) |
|---|---|---|---|
| 5 C[2] | 50:50 | 22 BA/75.5 MMA/2 MAA/ 0.5 ALMA | 41 EHA/32.5 MMA/2.5 STY/ 16 AAEM/8 MAA |
| 6 C | 50:50 | 22 BA/40.4 MMA/35.1 EA/ 2 MAA/0.5 ALMA | 41 EHA/32.5 MMA/2.5 STY/ 16 AAEM/8 MAA/0.29 MPA |
| 7 C | 60:40 | 62 BA/25.5 MMA/10 AAEM/2.5 MAA | 15 BA/40 MMA/45 STY |
| 8 C | 50:50 | 71.6 MA/23.9 MMA/4 MAA/0.5 ALMA | 41 EHA/32.5 MMA/2.5 STY/ 16 AAEM/8 MAA/0.29 MPA |
| 9 C | 50:50 | 22 BA/75.5 MMA/2 MAA/ 0.5 ALMA | 60 EA/13.5 MMA/2.5 STY/16 AAEM/8 MAA/0.29 MPA |
| 10 C | 75:25 | 22 BA/75 MMA/2 MAA/ 1 ALMA | 41 EHA/32.5 MMA/2.5 STY/ 16 AAEM/8 MAA/0.29 MPA |
| 11 | 50:50 | 22 BA/71 MMA/2 MAA/ 5 ALMA | 41 EHA/32.5 MMA/2.5 STY/ 16 AAEM/8 MAA/0.29 MPA |
| 12 | 50:50 | 22 BA/74 MMA/2 MAA/ 2 ALMA | 41 EHA/32.5 MMA/2.5 STY/ 16 AAEM/8 MAA/0.29 MPA |
| 13 | 50:50 | 22 BA/75 MMA/2 MAA/ 1 ALMA | 41 EHA/32.5 MMA/2.5 STY/ 16 AAEM/8 MAA/0.29 MPA |
| 14 | 50:50 | 22 BA/75.5 MMA/2 MAA/ 0.5 ALMA | 41 EHA/32.5 MMA/2.5 STY/16 AAEM/8 MAA/0.65 MPA |
| 15 | 50:50 | 22 BA/75.5 MMA/2 MAA/ 0.5 ALMA | 41 EHA/32.5 MMA/2.5 STY/ 16 AAEM/8 MAA/1.0 MPA |
| 16 | 50:50 | 22 BA/75.9 MMA/2 MAA/ 0.1 ALMA | 41 EHA/32.5 MMA/2.5 STY/ 16 AAEM/8 MAA/0.29 MPA |
| 17 | 50:50 | 22 BA/76.0 MMA/2 MAA | 41 EHA/32.5 MMA/2.5 STY/16 AAEM/8 MAA/1.0 MPA |
| 18 | 50:50 | 22 BA/75.5 MMA/2 MAA/ 0.5 ALMA | 41 EHA/19.8 EA/12.7 MMA/2.5 STY/16 AAEM/8 MAA/0.29 MPA |
| 19 | 50:50 | 22 BA/75.5 MMA/2 MAA/ 0.5 ALMA | 31 EHA/42.5 MMA/2.5 STY/ 16 AAEM/8 MAA/0.29 MPA |
| 20 | 50:50 | 22 BA/75 MMA/2 MAA/ 1 ALMA | 52.2 EHA/32.5 MMA/2.5 STY/ 12.8 MAA/0.29 MPA |
| 21 | 50:50 | 22 BA/58.5 STY/17.0 MMA/2 MAA/0.5 ALMA | 41 EHA/32.5 MMA/2.5 STY/ 16 AAEM/8 MAA/0.29 MPA |
| 22 | 40:60 | 45.6 BA/53.9 MMA/ 0.5 ALMA | 34.9 BA/47.2 MMA/15.3 AAEM/ 2.5 MAA |
| 23 | 50:50 | 22 BA/38 MMA/37.5 STY/ 2 MAA/0.5 ALMA | 41 EHA/32.5 MMA/2.5 STY/ 16 AAEM/8 MAA/0.29 MPA |
| 24 | 25:75 | 22 BA/75.5 MMA/2 MAA/ 0.5 ALMA | 41 EHA/32.5 MMA/2.5 STY/ 16 AAEM/8 MAA/0.29 MPA |

[1]Parts by weight core polymer per parts by weight shell polymer based on 100 parts by weight total polymer.
[2]Comparative Example 4

Comparative

A two phase polymer was prepared according to Example 4 in JP 06-298624A. The procedure for Example 3 was repeated except that Monomer Emulsion #1a consisted of 205 g styrene, 45 g of butyl acrylate, 83.32 g DI water, and 2.18 g SDS (23.0 weight percent active); and Monomer Emulsion #2a consisted of 117.5 g of methyl methacrylate, 112.5 g of 2-ethylhexyl acrylate, 10 g of methacrylic acid, 10 g of 2-hydroxyethylmethacrylate, 0.25 g t-dodecyl mercaptan, 83.32 g DI water, and 2.18 g SDS (23.0 weight percent active). During the last hold, the reaction mixture formed into a solid gel ball.

The multi-phase polymers useful in the present invention were evaluated for their effectiveness in nail coating compositions for forming films. The procedure used was as follows:

The polymer to be evaluated (test polymer) was formulated into the following nail coating composition in Table 3:

TABLE 3

Nail Coating Composition

| Ingredients | A (pbw) |
|---|---|
| Test Polymer (40% solids) | 77.2 |
| Dowanol ® DPM[3] | 4.6 |

TABLE 3-continued

Nail Coating Composition

| Ingredients | A (pbw) |
|---|---|
| Texanol ®[4] | 1.6 |
| Byk-80[5] | 0.3 |
| Aculyn ® 44[6] | 1.1 |
| Ammonium hydroxide (28 weight percent active) | 2.5 |
| DI Water | 12.7 |

[3]Registered trademark of Dow Chemical Company; Midland, Michigan.
[4]Registered Trademark of Eastman Chemical; Rochester, New York.
[5]Supplied by BYK-Chemie Corporation; Wallingford, Connecticut.
[6]Registered Trademark of Rohm and Haas Company, Philadelphia, Pennsylvania.

The formulation in Table 3 was prepared by diluting the polymer emulsion with half of the DI Water shown in Table 3. Then, the polymer solution was adjusted to a pH between 8 and 9 with the ammonium hydroxide. Dowanol DPM, Texanol and Byk-80 were combined and added to the stirring polymer solution dropwise over 10 minutes. The remaining water and Aculyn 44 were combined and added to the stirring polymer solution dropwise over 10 minutes.

The resulting nail coating composition was evaluated for film quality, removeability, and resistance to print, chipping, peeling, oil, and water. Commercially available colorless nail enamel called "Creme", marketed by Revlon, was used as a comparison. The following test methods were used to evaluate the nail coating composition:

Film quality was measured by evenly applying, with a small brush approximately 0.2 grams of the nail coating composition to be tested to a human nail. After drying for about 30 minutes, the film was observed for film clarity.

Clear (cl): Nail coating composition formed a smooth, continuous, clear film.
Crack (cr): Nail coating composition formed a cracked or opaque film.

Removeability was measured by evenly applying, with a small brush, approximately 0.2 grams of the nail coating composition to be tested to a human nail. After a minimum of 4 days, a cotton tip applicator was soaked with acetone based nail polish remover and rubbed on the nail coating. The ease of removeability was observed under a microscope and ranked as follows:

Easy: Film dissolves readily when treated with nail polish remover and is easily removed from nail with virtually no rubbing or force with the applicator.
Moderate Plus (Mod+): Film is removed from the nail by rubbing about 5 times with minimal force with the applicator.
Moderate (Mod): Film is removed as moderate plus, but with more force and rubbing.
Difficult (Dif): Film is difficult to remove from nail. A large dose of nail remover and a fair amount of force and repetition is required.

Chipping and Peeling was measured by evenly applying approximately 0.2 grams of the nail coating composition to be tested to a human nail with a small brush. The nail coating was dried for 24 to 36 hours. After drying, a metal spatula was used to try to chip and peel the film off the nail. The ease of chipping and peeling was observed under a microscope and ranked as follows:
Excellent (Ex): Film does not chip or peel from nail.
Good (G): Film is difficult to chip or peel from nail.
Fair (F): Film is chipped or peeled from nail with moderate effort.
Poor (P): Film is chipped or peeled easily from nail.

Print resistance was measured by evenly applying to a poly(methylmethacrylate) square approximately 5 cm by 5 cm in size, approximately 0.7 grams of the nail coating composition to be tested. The nail coating was dried for 24 hours at ambient temperature. After drying, cheesecloth was pressed onto the coating using the thumb and forefinger for about 5 seconds. The cheesecloth was removed and the coating was evaluated to see if an impression of the cheesecloth was made on the coating.

Ex: No imprint was made.
G: Barely noticeable imprint was made.
F: Slight imprint was made which lowered sheen or gloss.
P: Imprint made and compromised film continuity.

Oil resistance was measured by evenly applying to a poly(methylmethacrylate) square, approximately 5 cm by 5 cm in size, approximately 0.7 grams of the nail coating composition to be tested. The nail coating was dried for 24 to 36 hours at ambient temperature. After drying, the square was immersed in corn oil for about 1 hour and then removed and washed with soapy water. After drying the film was examined with a metal spatula for film softening or removal.

Ex: Film did not change.
G: Film was softened slightly with no reduction in gloss, sheen, or print resistance.
F: Film was softened, gloss and sheen were lower, and less resistant to print.
P: Film was partially removed.

Water resistance was measured by evenly applying to a poly(methylmethacrylate) square, approximately 5 cm by 5 cm in size, approximately 0.7 grams of the nail coating composition to be tested. The nail coating was dried for 24 to 36 hours at ambient temperature. After drying, the square was immersed in deionized water for about 1 hour, removed and dried under ambient conditions. After drying the film was examined with a metal spatula for film softening or removal.

Ex: Film did not change.
G: Film was softened slightly with no reduction in gloss, sheen, or print resistance.
F: Film was softened, gloss and sheen were lower, and less resistant to print.
P: Film was partially removed.

The results of evaluating the nail coating compositions are reported in Tables 4–6. In Table 4, Examples 27–34, show the effect of varying shell Mw and levels of crosslinking agent on nail coating composition performance. Comparative Example 26 and Examples 30–32 show that the shell polymer phase should preferably be soluble in THF. The difference in solubility of Comparative Example 26 and Examples 30–32 is due to Comparative Example 26 containing no chain transfer agent and Examples 30–32 containing at least 0.29 weight percent chain transfer agent. The shell polymer's solubility is an indication of the amount of high Mw polymer which would not be measured by gel permeation chromatography using the method herein. Examples 28–30 in Table 4 show that as the level of crosslinking agent is increased the resistance of the nail coating composition to print, peeling, chipping, oil or water increases.

Table 6 shows the effect of varying the weight ratio of core polymer phase to shell polymer phase. Multi-phase polymers containing at least one core polymer and at least one shell polymer (Examples 48–49) have a better balance of film properties in comparison to polymers containing only one polymer phase (Comparative Example 46). Compara-

TABLE 4

Effect if Crosslinking Agent and Shell Mw

| Example | Polymer from Example | Wt % x-lnk[7] | Mw Shell[8] | SF Polym[9] | SF Shell[10] | Flm[11] | Rem[12] | Print | Peel | Chip | Oil | H$_2$O |
|---|---|---|---|---|---|---|---|---|---|---|---|---|
| 25 C | Creme | — | — | — | — | cl | Easy | G | Ex | Ex | G | G |
| 26 C | 5 | 0.5 | — | 5.7 | 11.5 | cr | Mod | F | F | F | F | G |
| 27 | 11 | 5.0 | ≧300,000 | 11 | 100 | cl | Dif | Ex | Ex | Ex | Ex | Ex |
| 28 | 12 | 2.0 | ≧300,000 | 19.0 | 100 | cl | Dif | Ex | G | G | G | G |
| 29 | 13 | 1.0 | ≧300,000 | 19.0 | 100 | cl | Mod | Ex | Ex | Ex | Ex | Ex |
| 30 | 1 | 0.5 | ≧300,000 | 25.0 | 100 | cl | Mod | G | Ex | Ex | Ex | Ex |
| 31 | 14 | 0.5 | 124,206 | 32.0 | 100 | cl | Mod+ | Ex | Ex | G | G | G |
| 32 | 15 | 0.5 | 74,614[13] | 42.5 | 100 | cl | Mod+ | G | G | G | F | G |
| 33 | 16 | 0.1 | ≧300,000 | 46.0 | 100 | cl | Dif | G | Ex | Ex | Ex | Ex |
| 34 | 17 | 0.0 | 74.614[13] | 100 | 100 | cl | Mod | G | G | G | F | G |

[7]Weight percent crosslinking agent based on total weight of monomer in core.
[8]Weight average molecular weight of shell polymer phase.
[9]Soluble fraction of total polymer.
[10]Soluble fraction of shell polymer.
[11]Film quality formed from nail coating composition.
[12]Removeability of nail coating composition.
[13]Average of two measurements.

The examples in Table 5 show the effect on nail coating composition performance when varying the core and shell compositions of the multi-phase polymers. Examples 35–45 show that the multi-phase polymers should preferably have at least one core polymer phase having a Tg of at least 30. Examples 35–45 also show that the multi-phase polymers should preferably contain a hydrophobic monomer content of at least 2 weight percent in the core polymer phase and at least 3 weight percent in the shell polymer phase.

tive Example 46 has the same composition as the combined core and shell composition of Example 48. Table 6 also shows that polymers having a weight ratio of core polymer to shell polymer of 20:80 to 70:30, based on 100 total parts by weight of polymer are effective in forming films in an aqueous nail coating composition.

TABLE 5

Effect of Core and Shell Composition

| Example | Polymer from Example | Tg °C. core | Tg °C. shell | Wt % Phobe core[14] | Wt % Phobe shell[15] | Flm | Rem | Print | Peel | Clip | Oil | H$_2$O |
|---|---|---|---|---|---|---|---|---|---|---|---|---|
| 25 C | Creme | | | | | cl | Easy | G | Ex | Ex | G | G |
| 35 C | 6 | 21 | 15 | 22.0 | 43.5 | cl | — | — | — | — | — | — |
| 36 C | 7 | -3 | 64 | 62.0 | 60.0 | cl | Mod | F | F | G | P | G |
| 37 C | 8 | 36 | 15 | 0.0 | 43.5 | cl | Easy | G | P | F | F | P |
| 38 C | 9 | 56 | 15 | 22.0 | 2.5 | cl | Easy | F | F | G | F | P |
| 39 | 1 | 56 | 15 | 22.0 | 43.5 | cl | Mod | G | Ex | Ex | Ex | Ex |
| 40 | 18 | 56 | -0.5 | 22.0 | 43.5 | cl | Mod | | F | F | F | |
| 41 | 19 | 56 | 30 | 22.0 | 33.5 | cl | Easy | F | F | G | G | G |
| 42 | 20 | 56 | 15 | 22.0 | 54.7 | cl | Mod | G | G | G | G | G |
| 43 | 21 | 56 | 15 | 80.5 | 43.5 | cl | Mod+ | G | F | G | G | Ex |
| 44 | 22 | 24 | 27 | 45.6 | 34.9 | cl | Dif | F | G | G | F | G |
| 45 | 23 | 56 | 15 | 59.5 | 43.5 | cl | Dif | Ex | Ex | Ex | Ex | G |

[14]Total weight percent hydrophobic monomer in core based on total monomer weight in core.
[15]Total weight percent hydrophobic monomers in shell based on total monomer weight in shell.

TABLE 6

Effect on Core:Shell Weight Ratio

| Example | Polymer from Example | Wt Ratio core:shell[16] | Film | Rem | Print | Chip | Oil | H$_2$O |
|---|---|---|---|---|---|---|---|---|
| 46 C | 2 | 100:0 | cr | Dif | G | P | F | G |
| 47 C | 10 | 75:25 | cr | — | Ex | — | — | — |
| 48 | 1 | 50:50 | cl | Mod | G | Ex | Ex | Ex |
| 49 | 24 | 25:75 | cl | Mod+ | G | Ex | Ex | Ex |

[16]Parts by weight core polymer to parts by weight shell polymer based on 100 parts by weight polymer.

In order to determine the effect of chain transfer agent level on shell polymer Mw and solubility, the shell polymer was synthesized, without synthesizing the core polymer phase, using different levels of chain transfer agent. The method used for synthesizing the shell polymer was as follows:

To a 3 liter, 4 neck round bottom flask with overhead stirrer, coil condenser, nitrogen adapter and a thermocouple, were added 657.4 g DI water and 20.0 g SDS (23 weight percent active). This mixture was stirred and heated to 85° C. under a nitrogen sweep using a heating mantle. Next, to the flask was added 28 g of a monomer emulsion (ME) consisting of 135.0 g DI water, 12.0 g SDS (23 weight percent active), 146.3 g methyl methacrylate, 184.5 g 2-ethylhexlacrylate, 72.0 g acetylacetoxyethylmethacrylate, 36.0 g methacrylic acid, 11.2 g styrene, and mercaptopropionic acid in the amount shown in Table 7. Residual ME was rinsed into the flask with 20 g DI water. The nitrogen sweep was turned off, and to the flask was added an initiator solution consisting of 1.35 g ammonium persulfate in 20.0 g DI water, and a solution consisting of 1.4 g sodium carbonate in 40.0 g DI water. After the addition of the buffer solution, the reaction mixture was held at 85 ° C. for 5 minutes. After the hold, the remaining ME, and a separate initiator solution of 0.67 g ammonium persulfate in 67.3 g DI water were linearly cofed into the flask over 75 minutes. After the feeds were complete, residual ME was rinsed into the flask with 20.0 g DI water. The reaction mixture was held at 85° C. for 20 minutes and then cooled to 60° C. Following cooling to 60° C., the mixture was chased to remove residual monomer over a 15 minute time period. The mixture was then cooled to room temperature and neutralized with a solution of ammonium hydroxide (28 weight percent active).

The resulting shell polymer was analyzed for Mw and solubility in THF according to the procedures described herein. The Mw and solubility results are shown in Table 7:

TABLE 7

Effect of Chain Transfer Agent on Shell Polymer Mw

| Example | CTA Level[17] | Mw Shell | SF Shell |
|---|---|---|---|
| 50 C | 0.0 | — | 11.5 |
| 51 | 0.29 | >300,000 | 100 |
| 52 | 0.45 | 184,897 | 100 |
| 53 | 0.65 | 124,206 | 100 |
| 54 | 0.80 | 90,721 | 100 |
| 55 | 1.00 | 74,614[18] | 100 |

[17]Percent by weight mercaptopropionic acid based on total weight of monomer in shell polymer.
[18]Average of two measurements.

Aqueous nail coating compositions shown in Table 8 were evaluated for rheology properties. Viscosity, creep, and leveling were measured and are reported in Table 8. Table 8 shows Aculyn 46 worked particularly well as a rheology modifier.

The procedure used to prepare the compositions in Table 8 was the same as the procedure used for Composition A in Table 3.

Viscosity was measured using a Brookfield Model DV III Programmable Rheometer with a Spindle #4 at various revolution speeds.

Creep was measured by evenly applying a film of the nail coating composition to be tested onto the surface of a pre-cleaned glass microscope slide. The film was then air dried with the slide positioned vertically. After about 30 minutes, the film was evaluated visually and ranked as follows:

Ex: Smooth, clear, and level film (no creep).
Very Good (VG): Barely noticeable areas of different film thickness in the film.
G: Slight formation of ridges or uneven areas in the film.
F: Noticeable unevenness in film, especially toward the bottom of the film.
P: Unevenness and ridges in film everywhere.

Leveling was measured by applying a film of the nail coating composition to be tested onto the surface of a pre-cleaned glass microscope slide. The film was then air dried with the slide positioned horizontally. After about 30 minutes, the film was evaluated visually and ranked as follows:

Ex: Smooth, clear, and level film with no brushlines.
VG: Barely noticeable brushlines in film which can barely be felt.
G: Slight brushlines in film which are noticeable to the eye.
F: Noticeably uneven areas in film due to brushlines.
P: Heavy brushlines present in the film everywhere.

TABLE 8

Rheology Properties of Aqueous Nail Composition

| | Nail Coating Composition | |
|---|---|---|
| Ingredients | B (gms) | C (gms) |
| Test Polymer (40% active)[19] | 158.2 | 158.2 |
| Dowanol ® DPM | 9.5 | 9.5 |
| Texanol | 3.2 | 3.2 |
| BYK-80 | 0.7 | 0.7 |
| Aculyn 44[20] | 0.17 | — |
| Aculyn 46[20] | — | 2.2 |
| Ammonium hydroxide (28 wt % active) | 1.0 | 2.2 |
| DI Water | 13.82 | 22.0 |
| Leveling | G | Ex |
| Creep | F | Ex |
| Viscosity | | |
| 2.5 rpm | 400 | 960 |
| 15 rpm | 386 | 880 |
| 50 rpm | 384 | 644 |

[19]Test polymer for Compositions B–C is Example 15.
[20]Supplied by Rohm and Haas Company.

Table 9 shows that the polymers useful in the present invention are useful in pigmented or clear aqueous compositions. In Table 9, Compositions D and E were prepared according to the procedure used for Composition A, except that in Composition E, the pigment dispersion was added after the Texanol and Byk, but before the Aculyn 44 was added. The pigment dispersion in Composition E was prepared by gradually adding 5 grams of D&C Red #6 Barium Lake to a solution containing 20 grams of DI water, 0.5 grams of Acusol® 479N (registered trademark of Rohm and Haas Company), and Neodol® 23-6.5. The mixture was stirred with a homogenizer for 10 minutes. The compositions were evaluated according to the procedures used in Examples 25–49.

TABLE 9

Nail Coating Compositions

| Ingredients | Nail Coating Composition | |
|---|---|---|
| | D (gms) | E (gms) |
| Test Polymer (40% active)[21] | 158.0 | 158.2 |
| Dowanol ® DPM | 6.4 | 6.1 |
| Texanol | 3.2 | 3.1 |
| BYK-80 | 0.7 | 0.5 |
| Aculyn 44 | 0.7 | 1.3 |
| Ammonium hydroxide (28 wt % active) | 2.8 | 2.8 |
| DI Water | 27.0 | 21.0 |
| Pigment Dispersion | — | 5.0 |
| film quality | cl | cl |
| removeability | Mod+ | Mod+ |
| print resistance: | G | G |
| water resistance: | G | G |
| oil resistance: | Ex | Ex |

[21]Test polymer for Compositions D–E is Example 15.

We claim:

1. An aqueous nail coating composition comprising:
   at least one film forming agent comprising a dispersion of multi-phase polymers;
   wherein the multi-phase polymers comprise at least one inner polymer phase and at least one outer polymer phase;
   wherein the inner polymer has a Tg of at least 30° C. and comprises as polymerized units at least 2 weight percent of a hydrophobic monomer, based on total weight of monomer in the inner polymer;
   wherein the outer polymer has a Tg from −15° C. to 35° C., and comprises as polymerized units at least 3 weight percent of a second hydrophobic monomer; wherein the weight ratio of the inner polymer to the outer polymer is from 20:80 to 70:30; and
   provided that when the outer polymer has a weight average molecular weight equal to or greater than 200,000, the inner polymer further comprises at least 0.01 weight percent crosslinking agent based on total monomer in the inner polymer, and the outer polymer has a soluble fraction in tetrahydrofuran of at least 15 weight percent, and comprises from 3 weight percent to 70 weight percent of the second hydrophobic monomer based on total monomer in the outer polymer.

2. The aqueous nail coating composition of claim 1, wherein the weight average molecular weight of the outer polymer phase is less than or equal to 190,000.

3. The aqueous nail coating composition of claim 1, wherein the multi-phase polymers have a soluble fraction in tetrahydrofuran of at least 15 weight percent.

4. The aqueous nail coating composition of claim 1, wherein the inner polymer comprises at least 0.1 weight percent of the crosslinking agent.

5. The aqueous nail coating composition of claim 1, wherein the multi-phase polymers further comprise pendant acetoacetate groups.

6. The aqueous nail coating composition of claim 1, wherein the multi-phase polymers further comprise from 0.5 weight percent to 25 weight percent of at least one ethylenically unsaturated acid containing monomer.

7. The aqueous nail coating composition of claim 1, wherein the hydrophobic monomer is selected from the group consisting of $C_4$–$C_{10}$ .alkyl (meth)acrylates, aromatic vinyl compounds, and combinations thereof.

8. The aqueous nail coating composition of claim 1, wherein the crosslinking agent is selected from the group consisting of 1,4-butyleneglycol dimethacrylate, trimethylolpropane triacrylate, allyl methacrylate, diallyl phthalate, divinylbenzene, trivinylbenzene and combinations thereof.

9. The aqueous nail coating composition of claim 1, wherein the composition further comprises at least one coalescent agent.

10. The aqueous nail coating composition of claim 1, wherein the composition further comprises at least one hydrophobically modified nonionic ethoxylated urethane.

11. A method of coating nails comprising: applying the composition of claim 1 onto one or more nails.

12. A nail comprising the composition of claim 1.

* * * * *